United States Patent
Kitasaki et al.

(10) Patent No.: US 8,227,226 B2
(45) Date of Patent: Jul. 24, 2012

(54) METHOD FOR PRODUCING ENTRAPPING IMMOBILIZATION PELLETS, APPARATUS FOR PRODUCING THE SAME, AND ENTRAPPING IMMOBILIZATION PELLETS

(75) Inventors: Shoko Kitasaki, Tokyo (JP); Naoki Abe, Tokyo (JP); Tatsuo Sumino, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 70 days.

(21) Appl. No.: 12/805,830

(22) Filed: Aug. 20, 2010

(65) Prior Publication Data
US 2011/0045567 A1    Feb. 24, 2011

(30) Foreign Application Priority Data
Aug. 20, 2009 (JP) .................... 2009-191227

(51) Int. Cl.
*C12N 11/00* (2006.01)
(52) U.S. Cl. .................... 435/180; 435/174; 435/177
(58) Field of Classification Search .............. 435/174, 435/177, 180
See application file for complete search history.

(56) References Cited

U.S. PATENT DOCUMENTS
2006/0275885 A1 * 12/2006 Abe et al. .............. 435/252.1

FOREIGN PATENT DOCUMENTS
JP    2006-333851    12/2006

OTHER PUBLICATIONS

Water Treatment by Microorganism Immobilization method: Pellet Immobilization Method, Entrapping Immobilization Method and Biologically Activated Carbon Method, NTS Inc, 2000.
Tetsuo Sumino et al., Effects of Temperature and pH on characteristic of Immobilized Microorganisms Gel and Removal of High ammonium-nitrogen, Research division, 1991, pp. 755-762, vol. 14, No. 10.

* cited by examiner

*Primary Examiner* — David W Wu
*Assistant Examiner* — Vu A Nguyen
(74) *Attorney, Agent, or Firm* — Antonelli, Terry, Stout & Kraus, LLP.

(57) ABSTRACT

It is possible to eliminate fluctuation in the pellet strength of the entrapping immobilization pellets according to production lots, and constantly and stably produce the entrapping immobilization pellets having high pellet strength regardless of the production lots. An apparatus for producing entrapping immobilization pellets by polymerizing an immobilizing material into a gel in the presence of an activated sludge to entrap and immobilize microorganisms in the immobilizing material, the apparatus including: a line mixer which mixes an activated sludge with an immobilizing material to prepare a raw material solution, a temperature sensor which measures a temperature of the prepared raw material solution, an addition pump which adds a polymerization initiator to the prepared raw material solution, and a controller which controls the addition pump according to the measured temperature to control an additive rate of the polymerization initiator.

3 Claims, 5 Drawing Sheets

METHOD FOR PRODUCING ENTRAPPING IMMOBILIZATION PELLETS, APPARATUS FOR PRODUCING THE SAME, AND ENTRAPPING IMMOBILIZATION PELLETS

BACKGROUND OF THE INVENTION

1. Field of the Invention

The presently disclosed subject matter relates to a method for producing entrapping immobilization pellets, an apparatus for producing entrapping immobilization pellets, and entrapping immobilization pellets, and particularly relates to a technique to eliminate fluctuation in pellet strength of entrapping immobilization pellets according to production lots, thereby increasing pellet life span.

2. Description of the Related Art

Nitrifying bacteria included in an activated sludge used for waste water treatment grow slower than common bacteria. The number of the nitrifying bacteria decreases particularly in winter when a water temperature is low, leading to a significantly lower nitrification activity. This applies to useful bacteria whose proliferative rate is low as with the nitrifying bacteria. For that reason, waste water treatment performance is improved by immobilizing microorganisms containing useful bacteria such as the nitrifying bacteria, for example, an activated sludge in pellets to increase a concentration of such useful bacteria.

A method for immobilizing an activated sludge is mainly classified into the following two methods as described in "Biseibutsu-Koteikahouniyoru Mizushori, Tantai-Koteikahou, Houkatsu-Koteikahou, Seibutsu-Kasseitanhou [Water Treatment by Microorganism Immobilization Method: Pellet Immobilization Method, Entrapping Immobilization Method and Biologically Activated Carbon Method (in Japanese)]," published by NTS Inc., (2000). One is an attachment immobilization method (or a bonding immobilization method) in which an activated sludge is naturally attached or adsorbed to an inside of a surface or pores of pellets so that bacteria in the activated sludge proliferate. The other is an entrapping immobilization method for entrapping an activated sludge within an immobilizing material.

Comparing these two types of the immobilization methods, the entrapping immobilization method activates the useful bacteria such as the nitrifying bacteria more rapidly and more stably than the attachment immobilization method does. Entrapping immobilization pellets are produced by mixing an activated sludge with an immobilizing material such as a high molecular compound to prepare a raw material solution, and polymerizing this raw material solution by a polymerization initiator into a gel, as disclosed in Japanese Patent Application Laid-Open No. 2006-333851, for example.

SUMMARY OF THE INVENTION

However, even if the same immobilizing material and the same polymerization initiator are used for the entrapping immobilization pellets produced by the method described in Japanese Patent Application Laid-Open No. 2006-333851, the entrapping immobilization pellets show large fluctuation in the pellet strength according to production lots, and as a result, have substantially reduced pellet life span. In other words, a treatment tank for waste water treatment is packed with a large number of the entrapping immobilization pellets. Due to fluctuation in the pellet strength, however, the pellets need to be exchanged for new ones in accordance with the life span of the pellets having low pellet strength. This largely affects running cost of the waste water treatment. Thus, in order to increase the pellet life span, it is necessary to eliminate fluctuation in the pellet strength for every production lot, and to constantly produce the entrapping immobilization pellets having high pellet strength.

The presently disclosed subject matter has been made in consideration of such circumstances. An object of the presently disclosed subject matter is to provide a method for producing entrapping immobilization pellets, an apparatus for producing entrapping immobilization pellets, and entrapping immobilization pellets, by which it is possible to eliminate fluctuation in pellet strength according to production lots and to constantly and stably produce the entrapping immobilization pellets having high pellet strength regardless of the production lots, thereby increasing pellet life span during waste water treatment.

In order to achieve the object, a first aspect according to the presently disclosed subject matter provides a method for producing entrapping immobilization pellets which entraps and immobilizes microorganisms in an immobilizing material, by polymerizing the immobilizing material to gelate in the presence of the microorganisms, the method comprising: a raw material solution preparing step for mixing the microorganisms with the immobilizing material to prepare a raw material solution; a solution temperature measuring step for measuring a temperature of the prepared raw material solution; and an additive rate adjusting step for adjusting an additive rate of a polymerization initiator added to the prepared raw material solution, wherein in the additive rate adjusting step, the additive rate is adjusted according to the measured temperature so that the entrapping immobilization pellets to be produced have a ratio A/B ($kgf/cm^2$) which is a ratio of a compression stress at break A ($kgf/cm^2$) to a deformation ratio at break B (−), in a predetermined range.

The present inventors obtained knowledge that entrapping immobilization pellets having high pellet strength and long life span can be produced by adjusting an additive rate of a polymerization initiator according to a temperature of a raw material solution so that the raw material solution may form a gel securely and densely at a predetermined polymerization rate (polymerization speed) to enhance a crosslinking density of gel, not by adding a large amount of a polymerization initiator regardless of a temperature of a raw material solution so that the raw material solution may form a gel as a method for producing entrapping immobilization pellets conventionally performed. The present inventors obtained another knowledge that a ratio A/B ($kgf/cm^2$) which is a ratio of a compression stress at break A ($kgf/cm^2$) to a deformation ratio at break B (−) of the produced entrapping immobilization pellets can be used as an index whether gelling progresses securely and densely at the predetermined polymerization rate (polymerization speed), in order to evaluate progression of gelling exactly.

The presently disclosed subject matter has been devised on the basis of such knowledge. At the additive rate adjusting step, the additive rate of the polymerization initiator is adjusted according to a measured temperature so that the entrapping immobilization pellets to be produced have a ratio A/B ($kgf/cm^2$) of the compression stress at break A ($kgf/cm^2$) to the deformation ratio at break B (−) in a predetermined range. Thereby, the raw material solution can form a gel securely and densely at the predetermined polymerization rate to increase the crosslinking density of the gel. This can eliminate fluctuation in pellet strength of the entrapping immobilization pellets according to production lots, and stably and constantly produce the entrapping immobilization pellets having high pellet strength and long pellet life span regardless of the production lots.

The range of the ratio A/B is preferably from 5.5 to 25 kgf/cm$^2$, and more preferably from 12.5 to 21.5 kgf/cm$^2$. In this range, the pellet strength and pellet life span of the entrapping immobilization pellets can be improved.

In order to achieve the above-mentioned object, a second aspect according to the presently disclosed subject matter provides an apparatus for producing entrapping immobilization pellets which entraps and immobilizes microorganisms in an immobilizing material, by polymerizing the immobilizing material to gelate in the presence of the microorganisms, the apparatus comprising: a mixing device which mixes the microorganism with the immobilizing material to prepare a raw material solution; a solution temperature measurement device which measures a temperature of the prepared raw material solution; an addition device which adds a polymerization initiator to the prepared raw material solution; and an additive rate control device which controls the addition device according to the measured temperature, and controls an additive rate of the polymerization initiator. In the second aspect, the presently disclosed subject matter is configured as an apparatus.

In the apparatus for producing entrapping immobilization pellets according to the presently disclosed subject matter, in the additive rate control device, a correlation among the temperature, the additive rate, and the ratio A/B of the compression stress at break A (kgf/cm$^2$) to the deformation ratio at break B (-) of the produced entrapping immobilization pellets is set. The additive rate is preferably controlled on the basis of the correlation so that the ratio A/B may be from 5.5 to 25 kgf/cm$^2$. The ratio A/B is more preferably within the range of 12.5 to 21.5 kgf/cm$^2$.

In order to achieve the above-mentioned object, a third aspect according to the presently disclosed subject matter provides entrapping immobilization pellets which entraps and immobilizes microorganisms in an immobilizing material by polymerizing the immobilizing material to gelate in the presence of the microorganisms, wherein the entrapping immobilization pellets have a ratio A/B which is a ratio of a compression stress at break A (kgf/cm$^2$) to a deformation ratio at break B (-), and falls within a range from 5.5 to 25 kgf/cm$^2$.

In the third aspect, since the ratio A/B falls in a range from 5.5 to 25 kgf/cm$^2$, the entrapping immobilization pellets obtain increased pellet strength and pellet life span.

As described above, according to the presently disclosed subject matter, it is possible to eliminate fluctuation in pellet strength of the entrapping immobilization pellets according to production lots, and stably and constantly produce the entrapping immobilization pellets having high pellet strength regardless of the production lots. As a result, the pellet life span during waste water treatment can be increased.

DETAILED DESCRIPTION OF THE PREFERRED EMBODIMENTS

Hereinafter, according to the accompanying drawings, preferable embodiments of a method for producing entrapping immobilization pellets, an apparatus for producing entrapping immobilization pellets, and entrapping immobilization pellets according to the presently disclosed subject matter will be described in detail.

Figure 1:
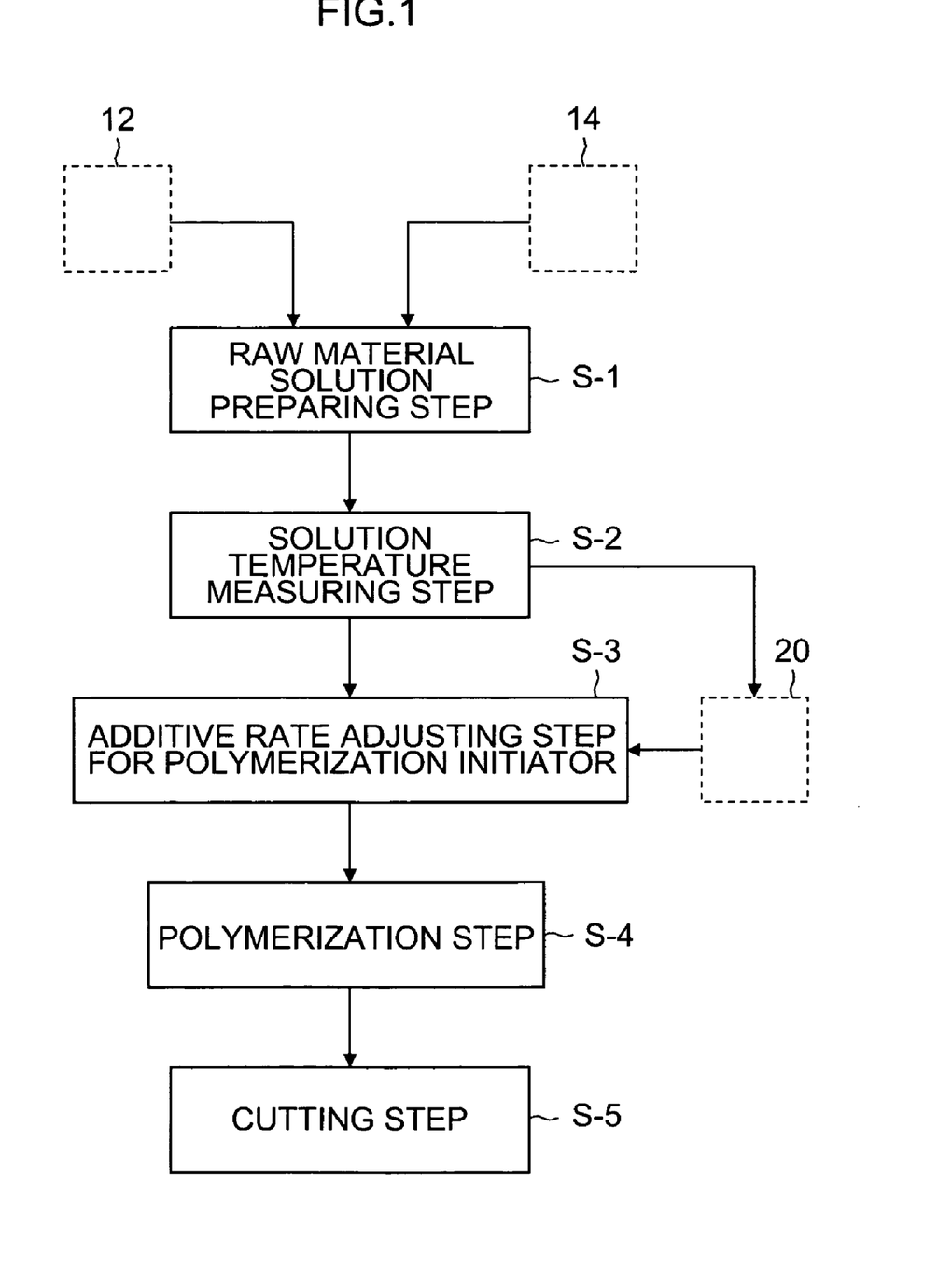
FIG. 1 is a step flow chart of a method for producing entrapping immobilization pellets according to the presently disclosed subject matter.
Figure 2:
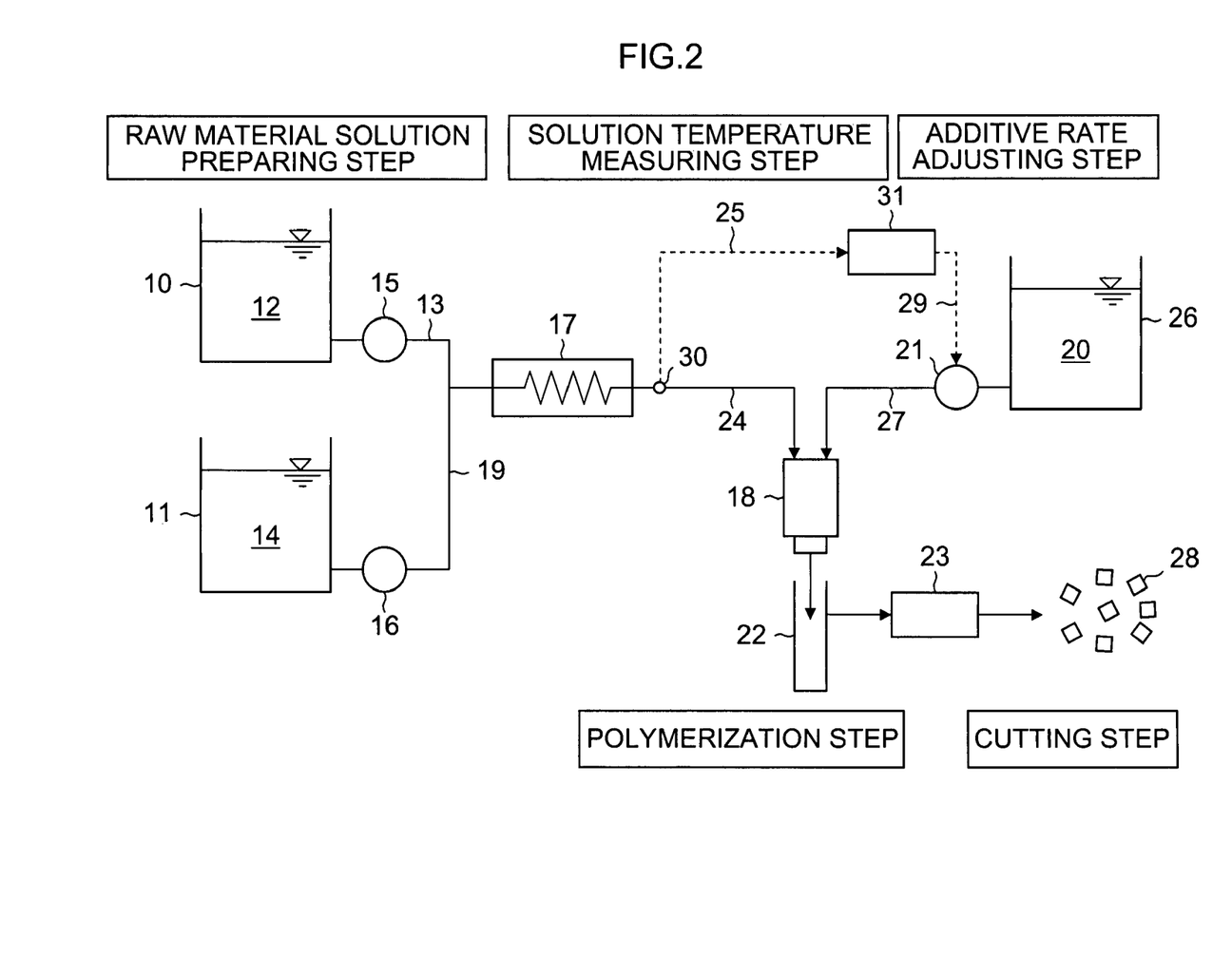
FIG. 2 is an entire configuration diagram showing an example of an apparatus for producing entrapping immobilization pellets according to the presently disclosed subject matter.

FIG. 1 shows a step flow of the method for producing entrapping immobilization pellets according to the presently disclosed subject matter, and FIG. 2 shows an example of an apparatus for producing entrapping immobilization pellets which performs the method for producing entrapping immobilization pellets.

As shown in FIG. 1, the method for producing entrapping immobilization pellets according to the presently disclosed subject matter comprises: a raw material solution preparing step (Step 1) of mixing an activated sludge 12 with an immobilizing material 14 to prepare a raw material solution; a solution temperature measuring step (Step 2) of measuring a temperature of the prepared raw material solution; an additive rate adjusting step (Step 3) for adjusting an additive rate of a polymerization initiator for polymerization according to the measured temperature; a polymerization step (Step 4) of polymerizing the raw material solution into a gel to form a predetermined shape; and a cutting step (Step 5) of cutting the obtained gel solid to obtain pellets having a predetermined size.

As shown in FIG. 2, at the raw material solution preparing step, the activated sludge 12 stored in an activated sludge tank 10 is sent to a line mixer 17 through a tube 13 by a first pump 15, and the immobilizing material 14 stored in a immobilizing material tank 11 is sent to the line mixer 17 through a tube 19 by a second pump 16. Thereby, the activated sludge 12 and the immobilizing material 14 are mixed in the line mixer 17 to prepare the raw material solution.

A device of mixing is the line mixer 17 in the embodiment, but not limited to this. Batch processing can also be performed using a stirring tank including stirring blades.

In the presently disclosed subject matter, the activated sludge 12 (the embodiment) including mixed microorganisms, such as nitrifying bacteria, denitrifying bacteria, and anaerobic ammonium oxidizing bacteria, can be suitably used as microorganisms entrapped and immobilized in the immobilizing material 14. In order to increase an immobilization initial concentration of the microorganisms, a concentration of the activated sludge is preferably 10000 to 40000 mg-SS/L. The above-mentioned microorganisms are not limited to the activated sludge 12, pure microorganisms, such as nitrifying bacteria, denitrifying bacteria, anaerobic ammonium oxidizing bacteria, BOD (biochemical oxygen demand) component oxidizing bacteria, bisphenol A decomposing bacteria, water bloom decomposing bacteria, PCB (polychlorinated biphenyl) decomposing bacteria, dioxin decomposing bacteria, and environmental hormone decomposing bacteria, can be used.

The immobilizing material 14 includes, but not particularly limited to, high-molecular monomers, prepolymers, and oligomers. For example, polyacrylamide, polyvinyl alcohol, polyethylene glycol, sodium arginate, carragheenan, and agar can be used.

The prepolymers can include monomethacrylates, monoacrylates, dimethacrylates, diacrylates, trimethacrylates, triacrylates, tetraacrylates, and urethane acrylates shown below.

(Monomethacrylates)

Polyethylene glycol monomethacrylate, polyprene glycol monomethacrylate, polypropylene glycol monomethacrylate, methoxy diethylene glycol methacrylate, methoxy polyethylene glycol methacrylate, methacryloyloxy ethyl hydrogen phthalate, methacryloyloxy ethyl hydrogen succinate, 3-chloro-2-hydroxypropyl methacrylate, stearyl methacrylate, 2-hydroxy methacrylate, ethyl methacrylate and so on.

(Monoacrylates)

2-hydroxyethyl acrylate, 2-hydroxypropyl acrylate, isobutyl acrylate, t-butyl acrylate, isooctyl acrylate, laurylacrylate, stearylacrylate, isobornyl acrylate, cyclohexyl acrylate, methoxy triethylene glycol acrylate, 2-ethoxyethyl acrylate, tetrahydrofurfuryl acrylate, phenoxy ethyl acrylate, nonylphenoxypolyethylene glycol acrylate, nonylphenoxypolypropylene glycol acrylate, silicon denatured acrylate, polypropylene glycol monoacrylate, phenoxy ethyl acrylate, phenoxydiethylene glycol acrylate, phenoxypolyethylene glycol acrylate, methoxy polyethylene glycol acrylate, acryloyloxyethyl hydrogen succinate, laurylacrylate and so on.

(Dimethacrylates)

1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanedioldimethacrylate, neopentyl glycol dimethacrylate, polyprene glycol dimethacrylate, 2-hydroxy-1,3-dimethacryloxy propane, 2,2-bis-4-methacryloxy ethoxy phenylpropane, 3,2-bis-4-methacryloxy diethoxy phenylpropane, 2,2-bis-4-methacryloxy polyethoxy phenylpropane and so on.

(Diacrylates)

Ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxy ethoxyphenyl propane, 2-hydroxy-1-acryloxy-3-methacryloxy propane and so on.

(Trimethacrylates)

Trimethylolpropane trimethacrylate and so on.

(Triacrylates)

Trimethylolpropane triacrylate, pentaerythritol triacrylate, trimethylolpropane EO-added triacrylate, glycerol PO-added triacrylate, and ethoxylated trimethylolpropane triacrylate.

(Tetraacrylates)

Pentaerythritol tetraacrylate, ethoxylated pentaerythritol tetraacrylate, propoxylated pentaerythritol tetraacrylate, ditrimethylolpropane tetraacrylate and so on.

(Urethane Acrylates)

Urethane acrylate, urethane dimethyl acrylate, urethane trimethyl acrylate and so on.

(Others)

Acrylamide, acrylic acid, and dimethylacrylamide.

As shown in FIG. 2, at the following solution temperature measuring step, a temperature of the raw material solution sent from the line mixer 17 to the mixer 18 is measured, and the measured value is sent to a controller 31. In other words, a temperature sensor 30 is provided in the course of a tube 24 which connects the line mixer 17 with the mixer 18, and the measured value measured by the temperature sensor 30 is sent to the controller 31 through a signal cable 25 or wireless communication. The controller 31 controls an addition pump 21 described later through a signal cable 29 or wireless communication. Any sensor may be used as the temperature sensor 30 as long as the sensor can measure the temperature of the raw material solution with sufficient accuracy.

On the other hand, at the additive rate adjusting step, a polymerization initiator 20 stored in a polymerization initiator tank 26 is sent to the mixer 18 through an addition tube 27 by the addition pump 21. Thereby, the raw material solution and the polymerization initiator 20 are mixed in the mixer 18, and a polymerization reaction of the raw material solution is started. The polymerization initiator 20 in the presently disclosed subject matter is not particularly limited as long as the polymerization initiator 20 is a reagent that can polymerize the raw material solution into a gel. Potassium persulfate can be suitably used for the polymerization initiator 20. A polymerization accelerator is preferably used in combination. β-dimethylamino propionitrile, NNN'N'-tetramethylethylene diamine, and the like can be preferably used. An amount of an amine based polymerization accelerator to be added is preferably within the range of 0.01 to 0.5% by mass based on the mixed solution (or pellets).

The mixer 18 is not particularly limited as long as the mixer is an apparatus which can uniformly mix the raw material solution with the polymerization initiator. For example, a single screw extruder including one screw shaft within a barrel or a twin screw extruder including two screw shafts within a barrel can be suitably used for the mixer 18.

Then, the mixed solution obtained by mixing the raw material solution with the polymerization initiator by the mixer 18 is charged from the mixer 18 into a forming frame 22. Within the forming frame 22, the mixed solution is polymerized thereby to be molded into a gel solid having a predetermined shape (for example, a rectangular block). A polymerization time in the forming frame 22 is from 1 to 60 minutes, and preferably from 1.5 to 60 minutes. Subsequently, the gel solid having a predetermined shape is cut into a pellet-like form having 3 mm squares (millimeter squares), for example, by a cutting device 23 at the cutting step. Thereby, entrapping immobilization pellets 28 having a pellet-like form are produced.

In the polymerization reaction of the raw material solution, when the polymerization initiator 20 is added to the raw material solution so that the raw material solution forms a gel, the crosslinking density of the gel largely influences pellet strength and pellet life span of the entrapping immobilization pellets 28. Accordingly, in order to improve the pellet strength and pellet life span of the entrapping immobilization pellets 28, it is important to progress gelling securely and densely at a predetermined rate of polymerization to increase the crosslinking density of the gel.

The present inventors found out that a ratio A/B (kgf/cm$^2$) of a compression stress at break A (kgf/cm$^2$) to a deformation ratio at break B (−) of the produced entrapping immobilization pellets can be used as an index whether gelling progresses securely and densely at the predetermined polymerization rate (polymerization speed), in order to exactly evaluate progression of gelling. In other words, the entrapping immobilization pellets 28 cannot obtain an increased gel crosslinking density when the ratio A/B is too large or too small, and, as a result, the entrapping immobilization pellets 28 having low pellet strength and short pellet life span are produced.

The ratio A/B used as the index of the pellet strength or pellet life span of the entrapping immobilization pellets 28 can be determined by performing a compression test on the produced entrapping immobilization pellets 28. Namely, using a Shimadzu Compact Table-Top Universal Tester EZ Test (made by Shimadzu Corporation), a disk having a diameter of 3 cm is moved downward in a perpendicular direction immediately from above the entrapping immobilization pellets 28 placed on a pressure plate at a speed of 5 mm/min. Then, the entrapping immobilization pellets 28 are compressed until the entrapping immobilization pellets 28 break. At that time, "strain" and "strength" of the entrapping immobilization pellets 28 are measured. The compression stress at break and the deformation ratio at break are determined by defining a point of time when a test force deteriorates rapidly as a point of time of break. The compression stress at break of the entrapping immobilization pellets 28 is a value obtained by dividing the maximum strength immediately before break by a compressed cross-section area of the entrapping immobilization pellets 28. The compression stress at break of the entrapping immobilization pellets 28 shows a difficulty of break (break-proofness) for the entrapping immobilization pellets 28, and can be an index of whether the pellet strength is "strong" or "weak."

On the other hand, the deformation ratio at break is a proportion of distortion of the entrapping immobilization pellets 28 immediately before break, and is represented by the following Formula 1:

Deformation ratio at break $(-)=(H0-H1)/H0$   (Formula 1)

wherein H0 indicates a pellet thickness before the pellets are compressed, and H1 indicates a pellet thickness immediately before break.

The deformation ratio at break of the entrapping immobilization pellets 28 can be used as an index of "ductile" or "brittle," which shows a degree of plasticity through which the entrapping immobilization pellets 28 break. From the deformation ratio at break, a difficulty of wear for the entrapping immobilization pellets 28 during waste water treatment can be known.

Figure 3:
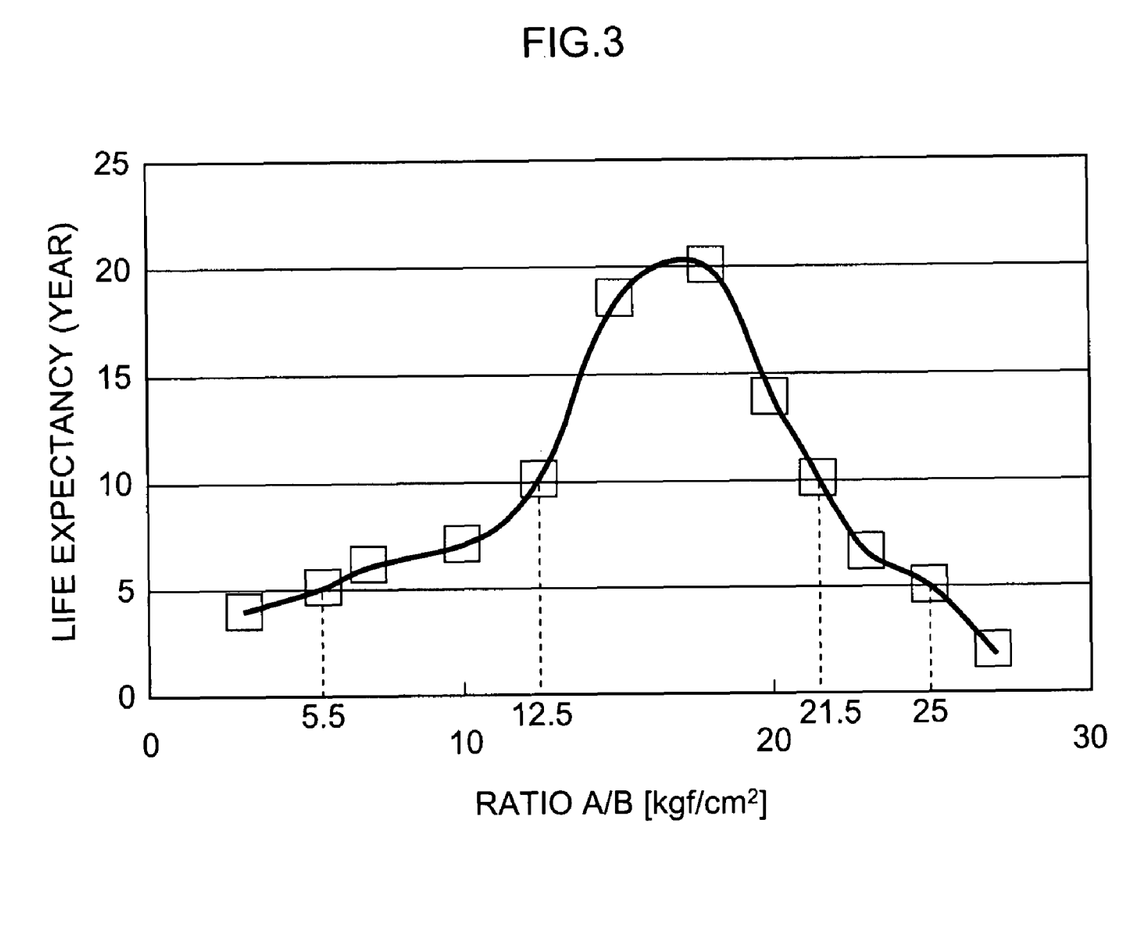
FIG. 3 is an explanatory diagram showing a relationship between a ratio A/B and life expectancy of entrapping immobilization pellets.

FIG. 3 shows a curve showing a relationship between the ratio A/B and life expectancy of the entrapping immobilization pellets 28. Here, the life expectancy refers to the pellet life span in a waste water treatment tank estimated by an accelerated aging test. The life expectancy is obtained by calculating a heating time until the compression stress at break reaches 1 kgf/cm$^2$ when the entrapping immobilization pellets 28 immersed in an adjusted solution of pH 8 (ordinary waste water is assumed) are subjected to thermal degradation (accelerated aging) at 121° C. and at 100° C., and by converting the calculated heating time into a time until the compression stress at break at 20° C., which is an average temperature during actual waste water treatment, reaches 1 kgf/cm$^2$ by the Arrhenius equation. As for the life expectancy, see Tatsuo Sumino et al., "Koteika Biseibutsu Perettono Choukianteiseito Kounoudo Anmoniasei Chissono Jokyo [Long-Term Stability of Microorganism Immobilized Pellets and Denitrification of High Level Ammonia (in Japanese)]", Suishitsu Odaku Kenkyu [Research on Water Pollution (in Japanese)], Vol. 14, No. 10, pp 755-762, (1991).

As shown in FIG. 3, the life expectancy of the entrapping immobilization pellets 28 is largely influenced by the ratio A/B. In the ratio A/B from 5.5 to 25 kgf/cm$^2$, not less than five years generally demanded for the pellet life span can be secured. In the ratio A/B from 12.5 to 21.5 kgf/cm$^2$, a critical curve is drawn and the life expectancy increases drastically. Moreover, in the ratio A/B from 12.5 to 21.5 kgf/cm$^2$, a very long life expectancy from 10 years to 20 years can be achieved.

The present inventors obtained another knowledge that the ratio A/B which largely relates to the pellet strength and pellet life span of the entrapping immobilization pellets 28 is largely influenced by the rate of polymerization, and no appropriate ratio A/B described above (5.5 to 25 kgf/cm$^2$, preferably 12.5 to 21.5 kgf/cm$^2$) can be obtained when the rate of polymerization is too fast or is too slow. In other words, a predetermined rate of polymerization in order to obtain a suitable ratio A/B exists, and at this predetermined rate of polymerization, gelling can progress securely and densely to increase the crosslinking density of the gel. Then, a polymerization temperature and the additive rate of the polymerization initiator are largely related to the rate of polymerization. The rate of polymerization is faster at a higher polymerization temperature, and the rate of polymerization is slower at a lower polymerization temperature. The rate of polymerization is faster at a higher additive rate of the polymerization initiator 20, and the rate of polymerization is slower at a lower additive rate thereof. Particularly, the rate of polymerization largely changes depending on the polymerization temperature, resulting in large fluctuation in the pellet strength and the pellet life span. In order to control the polymerization temperature to keep the rate of polymerization constant at the predetermined rate, high costs and energy for air conditioners are needed. On the other hand, adjustment of the additive rate of the polymerization initiator 20 according to the polymerization temperature to keep the rate of polymerization constant at the predetermined rate can be performed at relatively low cost.

Accordingly, in the presently disclosed subject matter, the temperature of the raw material solution is measured, and the additive rate of the polymerization initiator 20 added to the raw material solution is adjusted according to the temperature so that the ratio A/B may be from 5.5 to 25 kgf/cm$^2$. In other words, a correlation among the temperature of the raw material solution, the additive rate of the polymerization initiator 20 added to the raw material solution, and the ratio A/B of the produced entrapping immobilization pellets 28 is inputted into the controller 31. On the basis of this correlation, the controller 31 controls an amount of discharge from the addition pump 21, i.e., the additive rate of the polymerization initiator 20 so that the ratio A/B may be from 5.5 to 25 kgf/cm$^2$. More preferably, the controller 31 controls so that the ratio A/B may be from 12.5 to 21.5 kgf/cm$^2$.

Thus, it is possible to eliminate fluctuation in the pellet strength of the entrapping immobilization pellets 28 according to production lots, and constantly and stably produce the entrapping immobilization pellets 28 having high pellet strength regardless of the production lots. As a result, the pellet life span during waste water treatment can be increased.

In the embodiment, in order to control the amount of the polymerization initiator 20 to be added, the temperature of the raw material solution before addition of the polymerization initiator is measured. However, the polymerization temperature which influences the rate of polymerization is a temperature during polymerization, and reasonably, the temperature is preferably measured in a discharging part of the mixer 18 after addition of the polymerization initiator 20. On the other hand, in the embodiment, the amount of the polymerization initiator 20 to be added is small, and the temperature of the raw material solution influences the polymerization temperature more largely. Accordingly, it is considered that the polymerization temperature can be simultaneously controlled by controlling the temperature of the raw material solution.

While a block molding method using the forming frame is used as the method for molding the entrapping immobilization pellets, tube forming, dropping granulation, and sheet forming can also be used. While the presently disclosed subject matter has devised a configuration in which the additive rate of the polymerization initiator is changed according to the temperature of the raw material solution in order to obtain an appropriate ratio A/B, a method for changing the temperature of the raw material solution may be used if air conditioning energy and the like are ignored.

EXAMPLE

Figure 4:
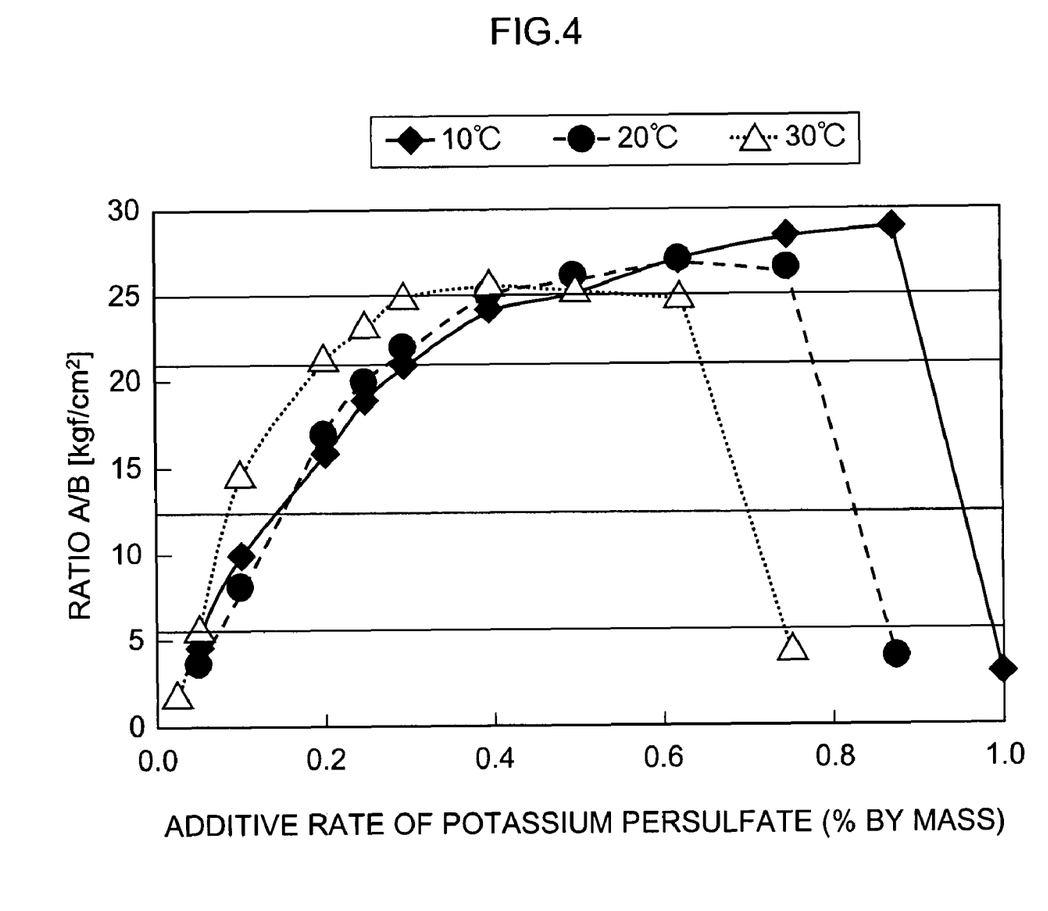
FIG. 4 is an explanatory diagram illustrating a relationship among a temperature of a raw material solution, an additive rate of potassium persulfate, and the ratio A/B.

FIG. 4 shows an example of the method for producing entrapping immobilization pellets according to the presently disclosed subject matter, in which the activated sludge 12, the immobilizing material 14, the polymerization initiator 20, and a polymerization accelerator shown in Table 1 were used, and a correlation among the temperature of the raw material solution, the additive rate of the polymerization initiator, and the ratio A/B when the raw material solution was polymerized into a gel was examined.

TABLE 1

| Composition | Description |
| --- | --- |
| activated sludge | MLSS 30000 mg/L |
| immobilizing material | polyethylene glycol methacrylate 10% by mass |
| polymerization initiator | potassium persulfate |
| polymerization accelerator | NNN'N' tetramethylethylene diamine 0.5% by mass |

In FIG. 4, the temperature of the raw material solution was three levels of 10° C., 20° C., and 30° C. An abscissa shows the additive rate of potassium persulfate (polymerization initiator), and an ordinate shows the ratio A/B.

As shown in FIG. 4, when the temperature of the raw material solution is 10° C., the ratio A/B can be controlled within the range of 5.5 to 25 kgf/cm$^2$ by adjusting the additive rate of potassium persulfate within the range of 0.06 to 0.5% by mass. Furthermore, the ratio A/B can be controlled within the more preferable range of 12.5 to 21.5 kgf/cm$^2$ by adjusting the additive rate of potassium persulfate within the range of 0.15 to 0.3% by mass.

When the temperature of the raw material solution is 20° C., the ratio A/B can be controlled within the range of 5.5 to 25 kgf/cm$^2$ by adjusting the additive rate of potassium persulfate within the range of 0.06 to 0.4% by mass. Furthermore, the ratio A/B can be controlled within the more preferable range of 12.5 to 21.5 kgf/cm$^2$ by adjusting the additive rate of potassium persulfate within the range of 0.15 to 0.27% by mass.

When the temperature of the raw material solution is 30° C., the ratio A/B can be controlled within the range of 5.5 to 25 kgf/cm$^2$ by adjusting the additive rate of potassium persulfate within the range of 0.06 to 0.3% by mass. Furthermore, the ratio A/B can be controlled within the more preferable range of 12.5 to 21.5 kgf/cm$^2$ by adjusting the additive rate of potassium persulfate within the range of 0.15 to 0.2% by mass.

Figure 5:
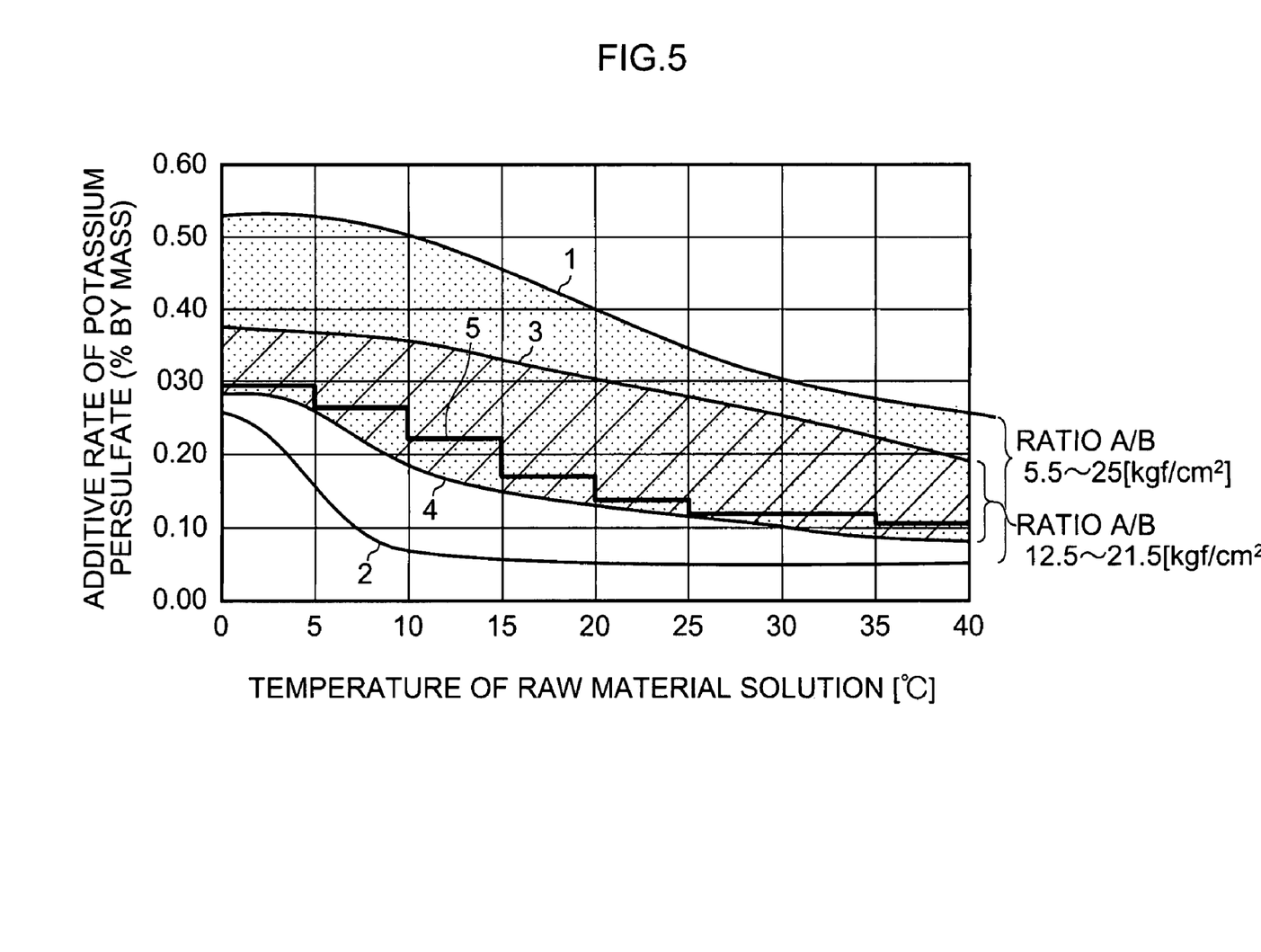
FIG. 5 is an explanatory diagram illustrating a relationship between a temperature of a raw material solution and an additive rate of potassium persulfate in order to ensure the ratio A/B in the presently disclosed subject matter.

FIG. 5 shows more detailed examination of a relationship between the temperature of the raw material solution and the additive rate of potassium persulfate in order to ensure the ratio A/B within the range of 5.5 to 25 kgf/cm$^2$ and within the more preferable range of 12.5 to 21.5 kgf/cm$^2$. The examination was performed at the temperature of the raw material solution from 0° C. to 40° C. in increments of 5° C. Curve 1 in FIG. 5 shows the upper limit of the range of the additive rate of potassium persulfate in which the ratio A/B is from 5.5 to 25 kgf/cm$^2$, and Curve 2 shows the lower limit thereof. Curve 3 shows the upper limit of the range of the additive rate of potassium persulfate in which the ratio A/B is from 12.5 to 21.5 kgf/cm$^2$, and Curve 4 shows the lower limit thereof.

As shown in FIG. 5, as the temperature of the raw material solution is increased, the range of the additive rate of potassium persulfate so that the ratio A/B ranges from 5.5 to 25 kgf/cm$^2$ shifts downward. Similarly, as the temperature of the raw material solution is increased, the range of the additive rate of potassium persulfate so that the ratio A/B ranges from 12.5 to 21.5 kgf/cm$^2$ shifts downward.

Accordingly, a stair-like control line 5 which shows the relationship between the temperature of the raw material solution and the additive rate of potassium persulfate is inputted to the controller 31, for example. Thereby, according to the temperature of the raw material solution, the additive rate of potassium persulfate can be controlled with sufficient accuracy so that the ratio A/B may fall in the range of 12.5 to 21.5 kgf/cm$^2$.

Thus, it is possible to eliminate fluctuation in the pellet strength of the entrapping immobilization pellets 28 according to production lots, and constantly and stably produce the entrapping immobilization pellets 28 having high pellet strength regardless of the production lots. As a result, the pellet life span during waste water treatment can be increased.

What is claimed is:

1. A method for producing entrapping immobilization pellets which entraps and immobilizes microorganisms in an immobilizing material, by polymerizing the immobilizing material to gelate in the presence of the microorganisms, the method comprising:
   a raw material solution preparing step for mixing the microorganisms with the immobilizing material to prepare a raw material solution;
   a solution temperature measuring step for measuring a temperature of the prepared raw material solution; and
   an additive rate adjusting step for adjusting an additive rate of a polymerization initiator added to the prepared raw material solution,
   wherein in the additive rate adjusting step, the additive rate is adjusted according to the measured temperature so that the entrapping immobilization pellets to be produced have a ratio A/B (kgf/cm$^2$) which is a ratio of a compression stress at break A (kgf/cm$^2$) to a deformation ratio at break B (-), in a predetermined range.

2. The method for producing entrapping immobilization pellets according to claim 1, wherein the additive rate of the polymerization initiator is adjusted so that the ratio A/B falls within a range from 5.5 to 25 kgf/cm$^2$.

3. The method for producing entrapping immobilization pellets according to claim 1, wherein the additive rate of the polymerization initiator is adjusted so that the ratio A/B falls within a range from 12.5 to 21.5 kgf/cm$^2$.

* * * * *